United States Patent [19]

Bailey

[11] Patent Number: 4,582,706

[45] Date of Patent: Apr. 15, 1986

[54] PREPARATION OF LIQUID LINAMENT

[76] Inventor: Byron H. Bailey, 409 Oakwood St. SE., Washington, D.C. 20032

[21] Appl. No.: 678,577

[22] Filed: Dec. 5, 1984

Related U.S. Application Data

[63] Continuation-in-part of Ser. No. 502,718, Jun. 9, 1983, abandoned.

[51] Int. Cl.$^4$ .............................................. A61K 35/78
[52] U.S. Cl. ................................................... 424/195
[58] Field of Search ...................................... 424/195.1

[56] References Cited

U.S. PATENT DOCUMENTS 177,614  5/1878  Battaglia .......................... 424/195.1
375,706  12/1887  Hoppel ............................. 424/195.1

*Primary Examiner*—Albert T. Meyers
*Assistant Examiner*—John W. Rollins
*Attorney, Agent, or Firm*—Jerome J. Norris

[57] ABSTRACT

An externally applied liquid linament massage composition consisting essentially of a ternary solution of an aliphatic alcohol having up to six carbon atoms, turpentine, camphor, and the soluble materials at room temperature from fresh fig leaves of Ficus Carica.

4 Claims, No Drawings

PREPARATION OF LIQUID LINAMENT

BACKGROUND OF THE INVENTION

This application is a continuation-in-part for my previous U.S. application, Ser. No. 502,718 filed June 9, 1983, now abandoned.

Numerous externally applied bath and linament preparations are known for use as rubbing or massage compositions to promote general circulation, and these compositions can be used at room temperature or in conjunction with externally applied heat. These preparations appear to reduce the acuteness of general aches and pain when externally applied in a massage-like or rubbing motion.

Accordingly, the need for effective, non-toxic, and non-harmful preparations of the linament type applied externally exists in good demand, and it is the principal object of this invention to satisfy this need in a substantial manner.

In accordance with the present invention, it has been discovered that the soluble materials of fresh fig leaves from Ficus Carica, when extracted at room temperature in a ternary solution of an aliphatic alcohol, turpentine, and camphor provides an excellent linament preparation for external application to the body as a massage or rubbing compound.

DETAILED DESCRIPTION

The liquid linament composition for use as a rubbing or massage compound consists in preferred embodiments of essentially a mixture of the following volumetric proportions:

160 oz. alcohol (Isopropyl)
1 oz. turpentine (gum spirits)
1 oz. liquid camphor
1 oz. crystalline camphor
10 average size fresh fig leaves of Calimyrna variety Preparation of the ingredients:

1. In a crock or mixing bowl of adequate size, the alcohol is introduced, and the turpentine is mixed in to form a binary solution. Liquid camphor and crystalline camphor are added gradually up to the point to avoid turbidity, but in sufficient amounts to obtain a ternary solution. These amounts are 1 ounce of each per 160 ounces of the alcohol.

2. Ten fresh fig leaves are immersed in the solution, and stirred vigorously for 2 to 3 minutes, and 3. The admixture is allowed to stand at room temperature (68° F.) for at least 48 hours.

4. The solution is decanted-off and then bottled.

Method for application of preparation to body:

1. Immerse part of or whole body in hot water (i.e. up to maximum temperature which can be tolerated) for about 15 minutes to a maximum time of 30 minutes.

2. Dry part of or whole body (depending upon where linament is desired to be applied as massage or rubbing compound).

3. Liberally pat on, massage or rub the linament over the desired area, allowing time for solution to soak into the skin.

4. Apply moist hot towel or towels to part of body on which linament has been applied until towel cools.

5. Continue application of hot towels as often as desired.

Preferably the application should be carried out at bedtime for greater comfort and general relaxation.

While isopropyl alcohol represents the preferred aliphatic alcohol in the context of the invention, it is not critical, and any alcohol having up to and including six carbon atoms will suffice; thus, methyl, ethyl, n-propyl, isopropyl, butyl, amyl and hexyl are equally useful as a component in the binary solution.

Turpentine (gum spirits) in the approximate amount of 1/160th by volume of said alcohol is the preferred amount; however, this too is not critical. The important consideration is that the amount of turpentine be miscible with the alcohol so as to maintain a binary solution.

Any of the fresh fig leaves from Ficus Carica, to include most specifically, the Kadota, Black Mission, Calimyrna and Caprifig will suffice, however, the Calimyrna is the most preferred and in the amount of approximately 10 average size leaves.

The addition of liquid camphor and crystalline camphor can be added respectively in sequence or together, as long as it is added gradually while stirring to the binary alcohol-turpentine solution up to amounts sufficient to form a ternary solution, but insufficient in amount to cause turbidity. Optimally, these are found to be about 1/160th by volume of the alcohol.

In actual use of the preparation according to the invention, it has been found that the general relaxation obtained from massage is substantial in degree and quite long-lasting.

While the invention has been described in specific terms, it is to be understood that minor changes in the linament proportions are possible without departing from the spirit or scope of the invention as defined by the claims hereinafter set forth.

What is claimed is:

1. A method for preparing a liquid linament comprising: (1) admixing about 160 oz. of an aliphatic alcohol having up to six carbon atoms with about 1 oz. of turpentine at room temperature to form a binary solution; (2) adding about 1 oz. of liquid camphor and about 1 oz. of crystalline camphor in amounts sufficient to avoid turbidity but adequate to provide a ternary solution; (3) immersing about 10 average size fresh fig leaves of Ficus Carica into said ternary solution at room temperature for a sufficient period to dissolve the Ficus Carica materials soluble in said ternary solution; and (4) decanting-off the solution.

2. The method of claim 1, wherein the alcohol is selected from the group consisting of methyl, ethyl, n-propyl, isopropyl, butyl, amyl and hexyl, and the Ficus Carica is selected from the group consisting of Kadota, Black Mission, Calimyrna and Caprifig.

3. A liquid linament consisting essentially of a ternary solution of about 160 oz. of an aliphatic alcohol having up to six carbon atoms, about 1 part of turpentine, about 1 oz. of liquid camphor, about 1 oz. of crystalline camphor and the soluble materials at room temperature from about 10 average size fresh fig leaves of Ficus Carica.

4. The linament of claim 3, wherein the alcohol is selected from the group consisting of methyl, ethyl, n-propyl, isopropyl, butyl, amyl and hexyl and the Ficus Carica is selected from the group consisting of Kadota, Black Mission, Calimyrna and Caprifig.

* * * * *

UNITED STATES PATENT AND TRADEMARK OFFICE
CERTIFICATE OF CORRECTION

PATENT NO. : 4,582,706
DATED : April 15, 1986
INVENTOR(S) : Byron H. Bailey

It is certified that error appears in the above-identified patent and that said Letters Patent is hereby corrected as shown below:

In Claim 3, line 58, cancel "11", and replace it with --1--.

Signed and Sealed this

Twenty-ninth Day of July 1986

[SEAL]

Attest:

Attesting Officer

DONALD J. QUIGG

Commissioner of Patents and Trademarks